United States Patent [19]

Dutta et al.

[11] 4,137,397
[45] Jan. 30, 1979

[54] ERYTHROMYCIN ALDOBIONATES

[75] Inventors: Sadhan K. Dutta; Sanat K. Basu, both of Calcutta, India

[73] Assignee: Registrar, Jadavpur University, Calcutta, India; a part interest

[21] Appl. No.: 691,833

[22] Filed: Jun. 1, 1976

[51] Int. Cl.$^2$ ............................................. C07C 17/08
[52] U.S. Cl. ...................................... 536/9; 424/180; 536/17; 536/115
[58] Field of Search ........................... 536/9, 103, 105; 204/78 R

[56] References Cited

U.S. PATENT DOCUMENTS 3,873,614    3/1975    Lamberti et al. .................... 536/105

OTHER PUBLICATIONS

Avrutskaya et al., "Electro synthesis . . . Nickel Electrodes", Sov. Electrochem (USA), vol. 9, No. 6, Jun. 1973.
Chem. Abst. Chem. Substance Index, vol. 84, p. 1946(cs), 1976, "Enythromycin".
Kolesinska, "Lactobionic Acid and its Salts", Chem. Abst., vol. 70, 1969, parg. 6523q.
Parker et al., "Solution Additive . . . Study", Chem. Abst., vol. 67, 1967, parg. 102720k.
Garrett, "Basic Model . . . Concentrations", Chem. Abst. vol. 84, 1976, parg. 54650q.
Websters Third International Dict. 1963, Springfield Mass. (Merriam Co.) C. Owens, p. 51.
Hale, "Simple Procedures", *Ion Exchanges in Org. & Biochemistry*, 1957, Interscience Publishers, NY p. 131.
Rodd, Chem. of Org. (Carbon) Cpds., vol. III, part A, 1954, Elsevier Publ. Co., NY p. 88.

*Primary Examiner*—Richard Raymond
*Attorney, Agent, or Firm*—Birch, Stewart, Kolasch and Birch

[57] ABSTRACT

This invention relates to a novel process for the preparation of Erythromycin aldobionates and novel Erythromycin maltobionates, Erythromycin Cellobionate and Erythromycin mellibionate. The said process comprises converting an alkali metal salt of aldobionic acid into free aldobionic acid, neutralizing the obtained aldobionic acid with Erythromycin base and finally recovering the Erythromycin aldobionate.

3 Claims, No Drawings

ERYTHROMYCIN ALDOBIONATES

PRIOR ART

Erythromycin is an antibiotic that has been successfully used in the treatment of a variety of bacterial infections. It is a complex basic compound that has a very poor solubility in water (2 mg/ml). Aqueous suspensions have a very bitter taste and hence, are unsuitable for oral administration. Erythromycin is also readily inactivated in acid medium. In order to improve upon the palatability and better stability of Erythromycin, various esters and salts have been prepared from time to time.

Amongst the Erythromycin aldobionates, Erythromycin lactobionate is already known. The same has hitherto been prepared by treating Erythromycin base with Lactobiono-δ-lactone solution. The preparation of Lactobiono-δ-lactone is a cumbersome process in that alkali metal salts are converted into δ-lactone which is further to be purified. This not only enhances the cost of production but is also time consuming.

OBJECTS OF THE INVENTION

An object of this invention is to propose a novel process for the preparation of Erythromycin derivatives, e.g. Erythromycin aldobionates.

Another object of the present invention is to propose a new process for the preparation of Erythromycin aldobionates which overcomes the disadvantages of the prior art process.

A still further object of the present invention is to propose a method for preparation of novel Erythromycin aldobionates such as Erythromycin maltobionate, Erythromycin cellobionate and Erythromycin mellibionate.

Still another object of the present invention is to propose a method for the preparation of Erythromycin aldobionates which would have good solubility in water, good biological activity, better stability and low toxicity.

DESCRIPTION OF THE INVENTION

According to this invention there is provided a process for preparing Erythromycin aldobionates which comprises converting a alkali metal salt of aldobionic acid by passing the said alkali metal salt of aldobionic acid through cationic exchangers, neutralizing the obtained aldobionic acid with an equivalent amount of Erythromycin base to obtain a solution containing Erythromycin aldobionate and finally recovering the Erythromycin aldobionate from the said solution.

Alkali metal salts of aldobionic acids used for the preparation of Erythromycin aldobionates of the present invention are prepared by subjecting aldobiose such as lactose, maltose to electrolytic oxidation in the presence of an alkali carbonate or bi-carbonate and the corresponding alkali bromide. As an example of an alkali carbonate and bi-carbonate, sodium carbonate or bi-carbonate, lithium carbonate/lithium bicarbonate may be used. Likewise, as an example of an alkali bromide, lithium bromide or potassium bromide may be used.

An aldobiose such as lactose or maltose, is electrolytically oxidised in the presence of the alkali metal carbonates/bicarbonates and alkali bromides to obtain the solution of alkali metal lactobionate, maltobionate, etc. The resulting solution is concentrated under reduced pressure to a thin syrup from which the salt is precipitated by adding 95% ethyl alcohol or isopropyl alcohol. The crude salt is dissolved in a minimum amount of hot water and then filtered through decolorizing carbon and the salt recrystallized by adding a suitable amount of the desired alcohol. The process is repeated 3–4 times to get the desired alkali salt in the pure state.

The obtained alkali metal salt of aldobionic acid is converted into aldobionic acid by passing the alkali metal salt of aldobionic acid through a cationic exchanger.

Aldobionic acid, thus obtained, is neutralized with an equivalent amount of Erythromycin base to obtain a solution containing Erythromycin salt i.e. Erythromycin aldobionate.

Finally, from the solution containing Erythromycin aldobionate, Erythromycin aldobionate is recovered.

The said recovery may be carried out by the following processes:
(i) the solution containing Erythromycin aldobionate is freeze-dried and Erythromycin aldobionate is finally obtained; or
(ii) the solution containing Erythromycin aldobionate is subjected to concentration under reduced pressure and thereby a thin syrupy mass is obtained which is dehydrated by keeping for about 2 hours over anhydrous sodium sulphate. To the dehydrated product cool dry ether is added and Erythromycin aldobionate is precipitated out which is dried over phosphorus pentoxide.

We shall now describe the present invention with reference to the accompanying examples which are given by way of illustration but do not restrict the scope of the invention.

EXAMPLE 1

Preparation of Sodium Lactobionate, (monohydrate)

100 gram Lactose
25 gm. $NaHC_3$ and 10 gm. NaBr
were dissolved in 800 ml. of water and electrolyzed by passing 2A current through carbon/graphite electrodes for 15 hours, filtering the resulting solution, concentrating under reduced pressure to a thin syrup and then precipitating the salt by adding 90% ethyl alcohol. The crude salt was again dissolved in a minimum amount of hot water, treated with decolorizing carbon and precipitated by adding twice the volume of ethyl alcohol (90%). The process was repeated 2–3 times to get a pure product. The yield was 85%. The melting point of the compound is 175° ± 1° C.; $[\alpha]_D^{25} = +22.3°$.

EXAMPLE 2

Preparation of Lithium Maltobionate, (trihydrate)

90 gm. Maltose
10 gm. Lithium Carbonate
8 gm. Lithium Bromide
were dissolved in 800 ml. of water and electrolyzed by passing 1 ampere current through carbon/graphite electrodes for 30 hours, filtering the resulting solution, concentrating under reduced pressure to a thin syrup and then precipitating the salt by adding isopropyl alcohol. The crude salt was again dissolved in a minimum amount of hot water, treated with decolorizing carbon and precipitated by adding an equivalent volume of isopropyl alcohol. The process is repeated 2–3 times to get a pure product. The yield was 85%. The melting point of the compound was 107° ± 1°; $[\alpha]_D^{30} = +97.4°$ ± 0.1°.

EXAMPLE 3

Preparation of Erythromycin Maltobionate 0.90 gm. of lithium maltobionate, trihydrate prepared by the method as given in Example (2) was dissolved in 2 ml. of water and was then transferred quantitatively to a cationic exchange column for the liberation of the free acid. Thereafter, 1.58 gm. of Erythromycin base was dissolved in 10 ml. of ethanol. To this solution was added the acid solution and it was stirred well for 1 hour. The reaction mixture is then freeze-dried. The sample was further dried over phosphorus pentoxide. The yield was more than 90%. M.P 140–145°, $[\alpha]_D^{30} = -14.5° \pm 0.5°$ (Concentration = 1.7% in 90% ethanol). The activity of the compound against S. Lutea was 867.0 mcg/mg., $\lambda_{(Max)}^{KBr} = 1600$ cm$^{-1}$ —COO$^-$.

EXAMPLE 4

Preparation of Erythromycin Maltobionate 0.88 gm. of lithium maltobionate, trihydrate prepared by a method as described in Example (2) was dissolved in 2 ml. of water and this was passed quantitatively through a cationic exchanger for the release of the free maltobionic acid. The volume of the eluate was 40 ml. This solution was then concentrated to 5-6 ml. under reduced pressure. 1.55 gm. of Erythromycin base was dissolved in 10 ml. of ethanol and this solution was then added to the acid solution with thorough stirring. After complete addition the reaction mixture was stirred well for 30 minutes. The product was then concentrated under reduced pressure to about 5 ml (Syrupy mass). To this concentrated syrupy mass 6 gm. of anhydrous sodium sulphate was added and left for 2 hours. The dried syrupy mass was then separated from sodium sulphate and the adhering mass was then washed with absolute alcohol. The solution was again concentrated under reduced pressure to about 5 ml and then precipitated out by the addition of chilled ether (10 vols.). The precipitate was filtered and washed with dry ether and finally dried over phosphorus pentoxide ($P_2O_5$). The yield was over 80%. The m.p. of the compound was: 140–145°, specific rotation, $[\alpha]_D^{30} = -14.5° \pm 0.5°$. (Concentration 1.7% in 90% ethanol). The activity against S Lutea was: 845.1 mcg/mg., $\lambda_{(max)}^{(KBr)} = 1600$ cm$^{-1}$ —COO$^-$.

EXAMPLE 5

Preparation of Erythromycin Lactobionate 0.80 gm. sodium lactobionate, monohydrate, prepared by a method as described in Example (1) was dissolved in 2 ml. of water and then passed quantitatively through the cation exchange column. The acid was eluted from the column, the total volume being 40 ml. This solution was then concentrated under reduced pressure to about 5-6ml. Then 1.50 gm. of Erythromycin base was dissolved in 5 ml of ethyl alcohol and the solution was added to the acid solution. It was then kept at 40° for 16 hours. The reaction mixture was then concentrated under reduced pressure into a syrupy mass and then 6 gm. of anhydrous sodium sulphate was added to it and allowed to stand for 4 hours. The syrupy mass was separated from sodium sulphate by filtration and the residue was washed with absolute alcohol. The product was again concentrated to about 5 ml. and then precipitated from chilled ether. The sample was then dried over phosphorus pentoxide ($P_2O_5$). The yield was above 80%. M.P. — 140°-142°; Specific rotation, $[\alpha]_D^{30} = -43.0 \pm 0.5$, (Concentration 1.7% in 90% ethanol).

EXAMPLE 6

Preparation of Erythromycin Lactobionate 0.80 gm. of Sodium Lactobionate prepared by a method as described in example (1) was dissolved in 2 ml. of water. This was then quantitatively transferred to the cation exchanger (containing Amberlite IR 120) and eluted for the liberation of the free lactobionic acid. Then 1.50 gm. of Erythromycin base was dissolved in 10 ml. of alcohol. The acid solution (40 ml) was then added to the Erythromycin base solution with continuous stirring for 1 hour. The reaction mixture was then freeze dried. The yield was above 85%. M.P. of the compound = 140°-142°; Specific rotation, $[\alpha]_D^{30} = -43.0 \pm 0.5$. (Concentration = 1.7% in 90% ethanol).

Minimum Inhibitory Concentration (MIC) MCG/ML against various organisms was found as under:

| ERYTHROMYCIN MALTOBIONATE $\frac{MIC}{MCG/ML}$ (Minimum Inhibitory Concentration) in | | | |
|---|---|---|---|
| Aerobacter aerogens. | Bacillus Subtilis. | Escheriacoli | Staph. Aur. |
| 0.7 | 0.8 | 2.5 | 1.7 |

What we claim is:
1. Erythromycin Maltobionate.
2. Erythromycin Cellobionate.
3. Erythromycin Mellibionate.